(12) United States Patent
Lou et al.

(10) Patent No.: US 10,028,717 B2
(45) Date of Patent: Jul. 24, 2018

(54) RECONSTRUCTING COMPUTED TOMOGRAPHY SCAN IMAGE

(71) Applicant: Shenyang Neusoft Medical Systems Co., Ltd., Shenyang (CN)

(72) Inventors: Shanshan Lou, Shenyang (CN); Han Zheng, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 148 days.

(21) Appl. No.: 14/863,466

(22) Filed: Sep. 24, 2015

(65) Prior Publication Data

US 2016/0089096 A1 Mar. 31, 2016

(30) Foreign Application Priority Data

Sep. 25, 2014 (CN) .......................... 2014 1 0498955

(51) Int. Cl.
| | | |
|---|---|---|
| *G06K 9/00* | (2006.01) | |
| *A61B 6/00* | (2006.01) | |
| *A61B 6/03* | (2006.01) | |
| *G06F 19/00* | (2018.01) | |

(52) U.S. Cl.
CPC ................ *A61B 6/52* (2013.01); *A61B 6/032* (2013.01); *A61B 6/488* (2013.01); *G06F 19/3481* (2013.01)

(58) Field of Classification Search
None
See application file for complete search history.

(56) References Cited

U.S. PATENT DOCUMENTS

| | | |
|---|---|---|
| 6,307,909 B1 | 10/2001 | Flohr et al. |
| 2004/0066911 A1 | 4/2004 | Hsieh et al. |
| 2007/0116344 A1 | 5/2007 | Hsieh et al. |
| 2009/0028288 A1 | 1/2009 | Horiuchi |

(Continued)

FOREIGN PATENT DOCUMENTS

| | | |
|---|---|---|
| CN | 1575760 A | 2/2005 |
| CN | 1781454 A | 6/2006 |

(Continued)

OTHER PUBLICATIONS

Zhenghan, Investigation on the Fully Three Dimensional Reconstruction Algorithms of Cone Beam Computed Tomography, China Doctoral Dissertations Full-text Database, Jun. 15, 2012, p. 33-52.

*Primary Examiner* — Atiba O Fitzpatrick
(74) *Attorney, Agent, or Firm* — Kilpatrick Townsend & Stockton, LLP

(57) ABSTRACT

A method for reconstructing a CT scan image, comprising: performing a first scan to acquire a first projection data, wherein the first scan is a scan that a subject is covered by a low dose X-ray beam in an axial plane; performing a second scan to acquire a second projection data, wherein the second scan is a scan that a target portion of the subject is covered by a high dose X-ray beam in the axial plane; determining a data filling point in the second projection data, wherein the data filling point is located in a truncated region; and filling the data filling point in the second projection data with a data from the first projection data which corresponds to the data filling point; and reconstructing a second scan image based on the filled second projection data.

14 Claims, 4 Drawing Sheets

(56) References Cited

U.S. PATENT DOCUMENTS

2009/0122954 A1    5/2009  Bruder
2012/0275673 A1   11/2012  Star-Lack et al.
2014/0050295 A1*   2/2014  Dennerlein ............ A61B 6/032
                                                    378/4

FOREIGN PATENT DOCUMENTS

| CN | 101405619 A | 4/2009 |
| CN | 101529275 A | 9/2009 |
| WO | 2005104038 A1 | 11/2005 |

* cited by examiner

RECONSTRUCTING COMPUTED TOMOGRAPHY SCAN IMAGE

The present application claims the priority to Chinese Patent Applications No. 201410498955.4, titled "RECONSTRUCTING COMPUTED TOMOGRAPHY SCAN IMAGE", filed with the Chinese State Intellectual Property Office on Sep. 25, 2014, which is incorporated herein by reference in its entirety.

BACKGROUND

The present disclosure is directed to computed tomography.

Neusoft Medical Systems Co., Ltd. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS' latest successful developments, such as 128 Multi-Slice CT Scanner System, Superconducting MRI, Linear Accelerator, and PET products, have led China to become a global high-end medical equipment producer. As an integrated supplier with extensive experiences in large medical equipment, NMS has been committed to the study of avoiding secondary potential harm caused by excessive X-ray irradiation to the subject during the CT scanning process.

As described below, conventional CT scanners have their inadequacies and limitations. It is desirable to have improved methods and systems for performing CT scanning.

BRIEF DESCRIPTION OF DRAWINGS

Features of the present disclosure are illustrated by way of an example and not limited in the following figure(s), in which like numerals indicate like elements, in which.

DETAILED DESCRIPTION

The present disclosure is directed to computed tomography.

In order to obtain a non-truncated project data, an X-ray beam may be substantially covered the subject (e.g., a patient) during clinical computed tomography (CT) scanning process. However, in practice, it may just obtain the projection data of the disease portion of the subject. If the whole subject is substantially covered by X-ray, not only causes waste of the X-ray dose but also causes harm to the subject due to excessive X-ray irradiation.

For simplicity and illustrative purposes, a disclosure is described by referring mainly to an example thereof. In the following description, numerous specific details are set forth in order to provide a thorough understanding of the disclosure of the application. It will be readily apparent however, that the disclosure may be practiced without limitation to these specific details. In other instances, some methods and structures have not been described in detail so as not to unnecessarily obscure the disclosure. As used herein, the terms "a" and "an" are intended to denote at least one of a particular element, the term "includes" means includes but not limited to, the term "including" means including but not limited to, and the term "based on" means based at least in part on.

Figures 1A, 1B:
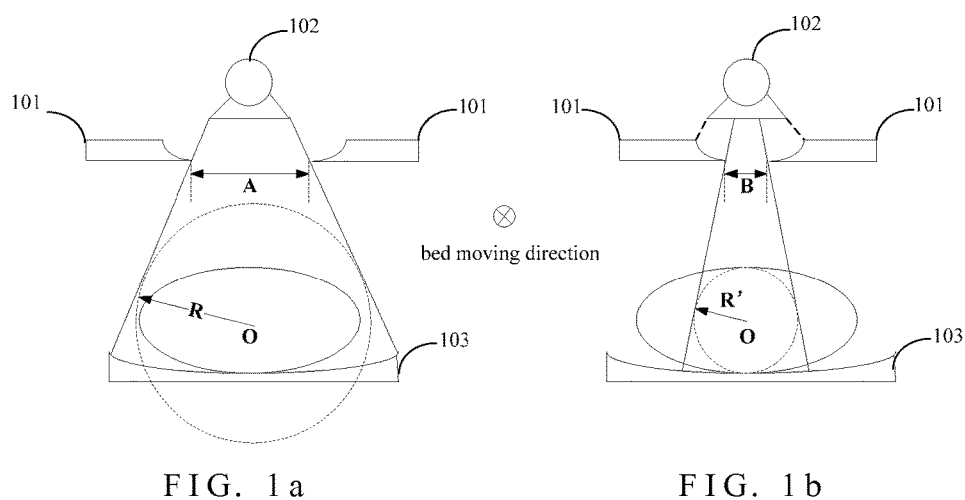
FIG. 1a is a schematic diagram showing that a subject is substantially covered by an X-ray beam in a sectional plane according to an example of the present disclosure.
FIG. 1b is a schematic diagram showing that a subject is partially covered by an X-ray beam in an axial plane according to an example of the present disclosure.

FIG. 1a and FIG. 1b are schematic sectional views perpendicular to the moving direction of the CT scanning bed, i.e., perpendicular to a line connecting the head and feet of the subject. And henceforth, the moving direction of the CT scanning bed is also called as bed moving direction or Z-axis direction.

In these examples, an X-ray beam from a source 102 is irradiated to the scanning bed 103 through a slit of a collimator 101. The X-ray source 102 is a member for generating an X-ray beam, typically including a high pressure tube and a corresponding control system. The collimator 101 is a set of moving members close to the X-ray source 102, and may change the width of the slit of the collimator 101 based on requirements, as shown in A and B of FIGS. 1a and 1b. An X-ray beam can be irradiated to the subject through the slit of the collimator 101, and the X-ray beam beyond the slit will be blocked by the collimator 101. The scanning bed 103 is a member for carrying the subject, and can move in accordance with the predetermined moving direction.

In these examples, the ellipse represents the axial plane of a subject; O represents the scan center of the CT scanner; a dashed circular region represents the X-ray irradiation range, i.e., a non-truncated region of a subject. As can be seen from FIG. 1a, the non-truncated region may substantially cover the subject in the axial plane, wherein the axial plane represents a plane perpendicular to the bed moving direction, and the subject may be substantially covered by an X-ray beam in the axial plane. After the X-ray source of the CT scanner emits an X-ray beam, the detector of the CT scanner will receive the X-ray beam and transform the X-ray beam into an electrical signal, such that a projection data may be formed and a reconstructed image for diagnosing the disease may be obtained based on the projection data.

FIG. 1b shows, when the X-ray beam may be irradiated to the subject through the narrowed slit of the collimator 101, the X-ray beam beyond the slit will be blocked by the collimator 101. In this way, the amount of X-ray beam irradiated to the subject is reduced and the X-ray dose can be saved. However, it may lead to another issue. The projection data of the region outside the circle having a radius of cannot be obtained, that is, a truncation may occur in the projection data. In practice, once a truncation occurs in the projection data, a truncated artifact may occur during the process of reconstructing CT scan image, wherein the truncated artefact represents various types of images originally not existing in the subject but appearing in the reconstructed image. The truncated artefact may lead to distorted images, abnormal CT values, which may mislead doctor's diagnosis.

It is thus to be appreciated that examples of the present disclosure provide an improved technique for reconstructing CT scan image. More specifically, previous projection data of the same subject in the scanning sequence may be used to fill the truncated region of a small view CT projection data (that is, the region outside the circle having a radius of R' shown in FIG. 1b) in order to obtain more accurate reconstruction images.

Generally, a clinical CT scan process may include a plurality of different scan sequences, wherein different scan sequences may be associated with different X-ray doses. A coronary CT examination, for an example, often contains two or more scan sequences, such as a pilot image sequence, a calcium scoring sequence, a contrast medium tracking pilot sequence, a contrast medium concentration tracking sequence, a coronary scan sequence, and so on. In order to obtain a non-truncated projection data of the heart, it may be necessary for the X-ray beam to substantially cover the subject. To lower the irradiation dose of X-ray received by the subject during the CT scan sequence, a small view X-ray scan may be used for some of the sequences. More specifically, the X-ray beam does not completely cover the subject in the range perpendicular to a line connecting the head and feet of the subject. As described in the present disclosure, in order to overcome a truncated artifact resulted from the small view scan, an earlier projection data generated before this small view scan sequence may be adopted to fill the truncated position of the projection data generated in this scan sequence. Since the previous projection data is filled into the truncated position of the current projection data, effects of truncated artifacts for a resultant reconstructed image can be avoided, which can improve the quality of the reconstructed image while reducing X-ray irradiation dose received by the subject.

Figure 2:
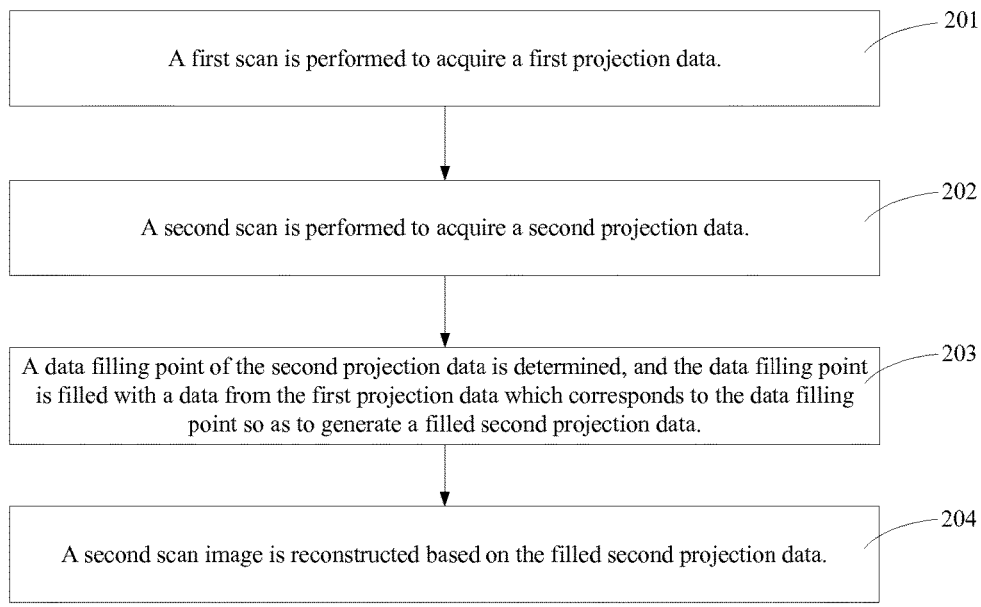
FIG. 2 is a schematic flowchart illustrating the procedures of a method for reconstructing CT scan image according to an example of the present disclosure.

FIG. 2 shows a method for reconstructing CT scan image is proposed according to an example of the present disclosure, and the method may include:

At block 201, a first scan is performed to acquire a first projection data, wherein the first scan is a scan that a subject is substantially covered by a relatively low dose X-ray beam in an axial plane.

In general, upon the information about the subject, the region to be scanned, and the position for the subject on the bed are determined, a low dose X-ray scan may be performed on the substantially whole subject in the axial plane, such as, a subject pilot scan or a contrast medium pilot scan. At this time, the width of the slit of the collimator 101 is set at width that an X-ray beam may substantially cover the whole subject in the axial plane, as is shown in FIG. 1a.

Wherein, the subject pilot scan is used for positioning the location of the subject on the bed so as to determine the scanning region. The contrast medium is a chemical injected or oral administered into tissues or organs of the subject for enhancing observed effects of images, and the density of the contrast medium is above or below the surrounding tissues. After performing the contrast medium pilot scan, these tissues, originally not appeared, will be presented in the image for helping a doctor to make a diagnosis.

It should be understood that, in this example, the subject is substantially scanned in the axial plane means that the subject is substantially complete in the plane perpendicular to the bed moving direction (i.e., X-Y plane), and does not limit whether the subject is complete in Z-axis.

Furthermore, in practice, after the first projection data is acquired, the first projection data may need some correction, wherein the correction is used for eliminating an artifact resulted from inaccuracies of the first projection data itself.

At block 202, a second scan is performed to acquire a second projection data, wherein the second scan is a scan that a target region of the subject is covered by a relatively high dose (compared to that of the earlier scan performed at block 201) X-ray beam in the axial plane.

According to the actual situation of the subject, the operator may need to determine a target region of the subject based on the first projection data acquired in the first scan, wherein the target portion may be usually the region most likely exhibiting lesion characteristics, or the so-called region of interest (ROI). If the operator wants to focus on observing the target region of the subject and reduce harm lead to the subject due to the X-ray irradiation, a narrower slit of the collimator 101 may be selected, and thus the X-ray beam may just emits to the target region, for example, the heart or brain of the subject, and so on.

It should be understood that, in practice, after the second projection data is acquired, the second projection data may need correction and reconstruction, wherein the correction is used for eliminating artifact(s) resulted from inaccuracies of the second projection data itself, and the reconstruction may be used for arranging the corrected projection data according to the required manner for reconstructing image.

At block 203, a data filling point of the second projection data is determined, and the data filling point is filled with data from the first projection data that correspond to the data filling point so as to generate a filled second projection data, wherein the data filling point is located in a truncated region.

In this example, the truncated region represents a region which is beyond the second scan range and may be appeared a truncated artifact while reconstructing a CT scan image with the second projection data. As shown in FIG. 1b, the truncated region indicates the region outside the dashed circle and inside the ellipse.

In the conventional scanning techniques, due to all data of the data filling point within the truncated region is set to zero, truncated artifacts usually appear on the CT scan image reconstructed by the second projection data, which may affect the doctor's diagnosis.

In this example, assuming that the absolute positions of a data filling point in different scans are the same, the data corresponding to the data filling point of the second projection data may be acquired from the first projection data and then filled into the data filling point of the second projection data. The so-called absolute position means that the relative positional relationship of the position with respect to a reference point is fixed, and the reference point is stationary with respect to the ground during the X-ray scan, for example, any point of the CT scanner gantry or photography that is stationary with respect to the ground.

At block 204, a second scan image is reconstructed based on the filled second projection data.

In this example, the data of the first projection data in the axial plane may be correspondingly filled to the data filling point within the truncated region of the second projection data, such that the second projection data in the axial plane may be changed from a projection data of the target region of the subject to a projection data of the substantially whole subject. Therefore, the possibility of generating a truncated artefact in the reconstructed second scan image may be effectively eliminated, which can improve the quality of the reconstructed scan image while reducing the X-ray dose received by the subject.

Figure 3:
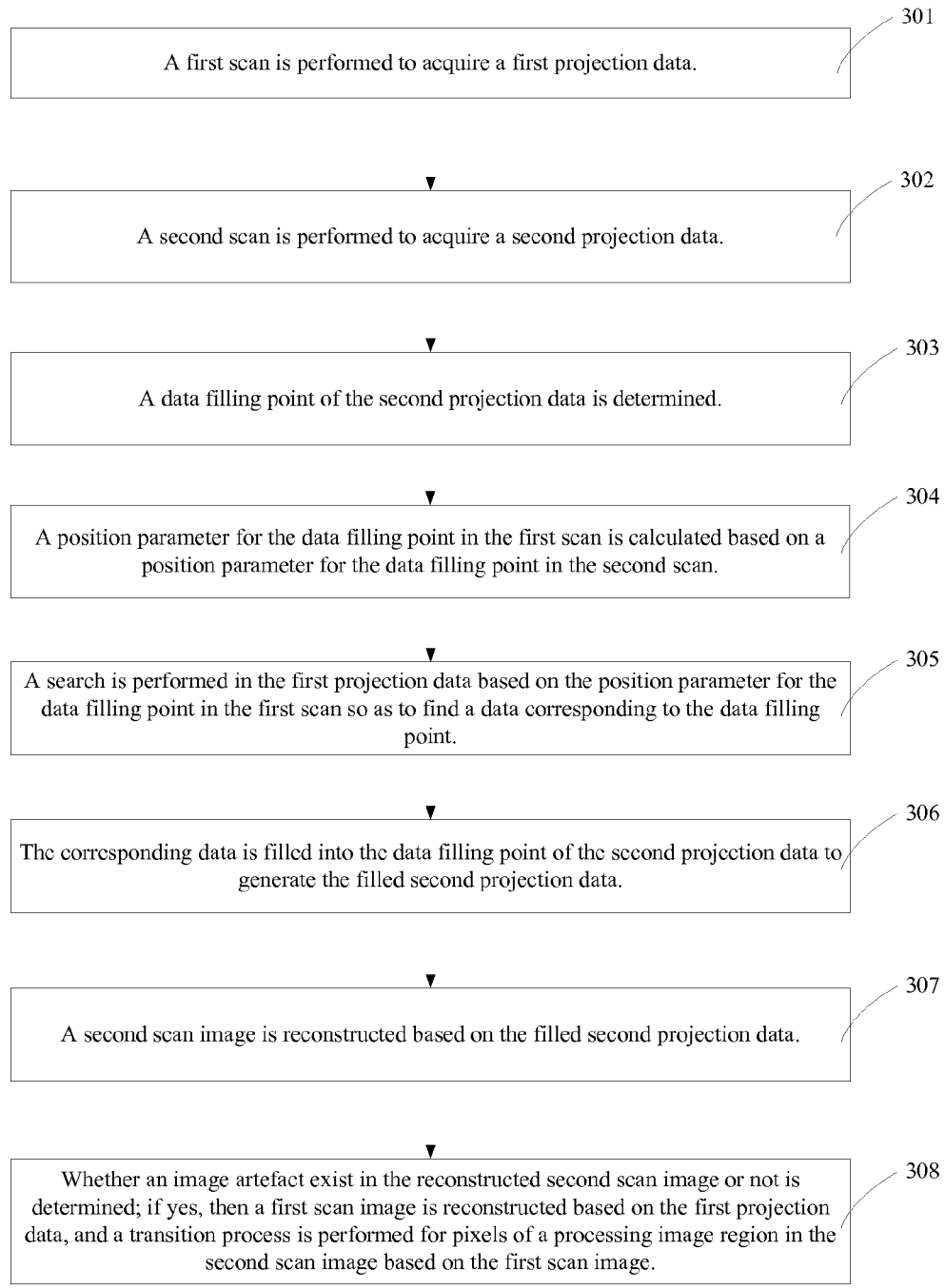
FIG. 3 is schematic flowchart illustrating the procedures of a method for reconstructing CT scan image according to another example of the present disclosure.

The first scan and the second scan may be different types of scan protocols, for example, the first scan may be an axial scan, and the second scan may be a helical scan. The so-called axial scan represents a scan that the scanning bed is fixed during the X-ray scan process, wherein the X-ray source surrounds the subject to perform a circular scan. The so-called helical scan represents a scan that the scanning bed carrying the subject to move forward and backward during the X-ray scan process, wherein a spiral motion exists between the X-ray source and the subject. In the examples of the present disclosure, the scan types of the first scan and the second scan are not limited. Therefore, the position parameters of the same data filling point in the first scan and the second scan may be different. Although the first scan and the second scan belong to the same scan type, the position parameters of the same data filling point in CT scans of different times or for different regions may be different. Please refer to FIG. 3. FIG. 3 is flowchart illustrating the procedures of a method for reconstructing CT scan image according to another example of the present disclosure. The method includes the following blocks.

At block 301, a first scan is performed to acquire a first projection data, wherein the first scan may be a scan that a subject is substantially covered by a relatively low dose X-ray beam in an axial plane.

At block 302, a second scan is performed to acquire a second projection data, wherein the second scan may be a scan that a target region of the subject is covered by a relatively high dose X-ray beam in the axial plane.

At block 303, a data filling point of the second projection data is determined, wherein the data filling point is located in a truncated region of a target region of the subject.

At block 304, a position parameter for the data filling point in the first scan is calculated based on a position parameter for the data filling point in the second scan.

In this example, the position parameter may include, but is not limited to, a channel index and a slice index of the axial plane. In practice, the position parameter can be set based on actual situations and requirements.

The position coordinate for the data filling point in the axial plane of the second scan is (c,r), wherein c indicates a second channel index and r indicates a second slice index.

The position coordinate for the data filling point in the axial plane of the first scan is (Ac, Ar), wherein Ac indicates a first channel index and Ac indicates a first slice index.

The (Ac, Ar) is obtained according to the following formulas:

$$ChannelPara = (c - MidC) \times \Delta c;$$

$$Ac = \begin{cases} \dfrac{ChannelPara}{\Delta c} + MidC & \beta' = \beta \\ \dfrac{-ChannelPara}{\Delta c} + MidC & \beta' = \beta \pm \pi \end{cases};$$

$$As = Z_{Channel} + (r - MidR) \times \Delta R;$$

$$Ar = \dfrac{As - Z_1}{\Delta RAxl} + MidAxlR.$$

Wherein the MidC indicates the center channel index of a detector; the $\Delta c$ indicates a channel interval; the ChannelPara indicates a distance between a channel in that the data filling point is located and a center channel of the detector; the β indicates a projection angle of the X-ray beam in the second scan; the β' indicates a projection angle of the X-ray beam in the first scan. The ray paths of the X-ray beam may be different in different scans. If the ray path of the X-ray beam in the first scan is the same as the ray path of the X-ray beam in the second scan, $\beta'=\beta$; if the ray paths of the X-ray beam are different in the first scan and in the second scan, $\beta'=\beta+\pi$ or $\beta'=\beta-\pi$.

The $Z_0$ indicates Z-axis coordinate of a projection center of the detector; the $Z_{Channel}$ indicates Z-axis offset representing a distance from the data filling point to the projection center of the detector; the MidR indicates a center slice index of the second scan; the AR indicates a slice interval of the second scan; the As indicates an intermediate variable; the $Z_1$ indicates Z-axis coordinate of the tomography in the first scan that is nearest the data filling point; the MidAxlR indicates a center slice index of the first scan; and the ΔRAxl indicates a slice interval of the first scan.

In an example, when the scan type is a helical scan, Z-axis offset $Z_{Channel}$ is calculated according to the following formulas:

$$Z_{Channel} = Z_0 + h \times \arcsin \dfrac{ChannelPara}{R};$$

$$h = \dfrac{DetW \times Pitch}{2\pi} \times BedDirection;$$

$$BedDirection = \begin{cases} 1 (foward) \\ -1 (backward) \end{cases}.$$

Herein, the $Z_0$ indicates Z-axis coordinate of the projection center of the detector; the h indicates a bed moving distance that the helical scan scans per 360-degree rotation; the R indicates a scanning radius of the helical scan; the DetW indicates a width of the detector in Z-axis direction; the Pitch indicates a pitch of the helical scan; and the BedDirection indicates an intermediate variable of a bed moving direction of the helical scan.

At block 305, a search is performed in the first projection data based on the position parameter for the data filling point in the first scan so as to find a data corresponding to the data filling point.

At block 306, the corresponding data is filled into the data filling point of the second projection data to generate the filled second projection data.

At block 307, a second scan image is reconstructed based on the filled second projection data.

A method for filling the data filling point within the truncated region of the second projection data is provided in this example, that is: calculating a position parameter for the data filling point in the first scan based on a position parameter for the data filling point in the second scan; performing a search in the first projection data based on the position parameter for the data filling point in the first scan so as to find a corresponding data; and filling the corresponding data into the data filling point of the second projection data to generate the filled second projection data.

Furthermore, in practice, if the scan types of the first scan and the second scan are different, their ray paths and projection angles of the X-ray beams may be different, and the data filled to the data filling point may not be able to match the second projection data. In this case, the reconstructed second scan image may have some artefact, however, the artefact is not so-called truncated artefact. For eliminating the artefact appeared in the second scan image in this case, on the basis of the above blocks 301-307, the example may further include the following step.

At block 308, whether an image artefact exist in the reconstructed second scan image or not is determined; if yes, then a first scan image is reconstructed based on the first projection data, and a transition process is performed for pixels of a processing image region in the second scan image based on the first scan image.

Figure 4:
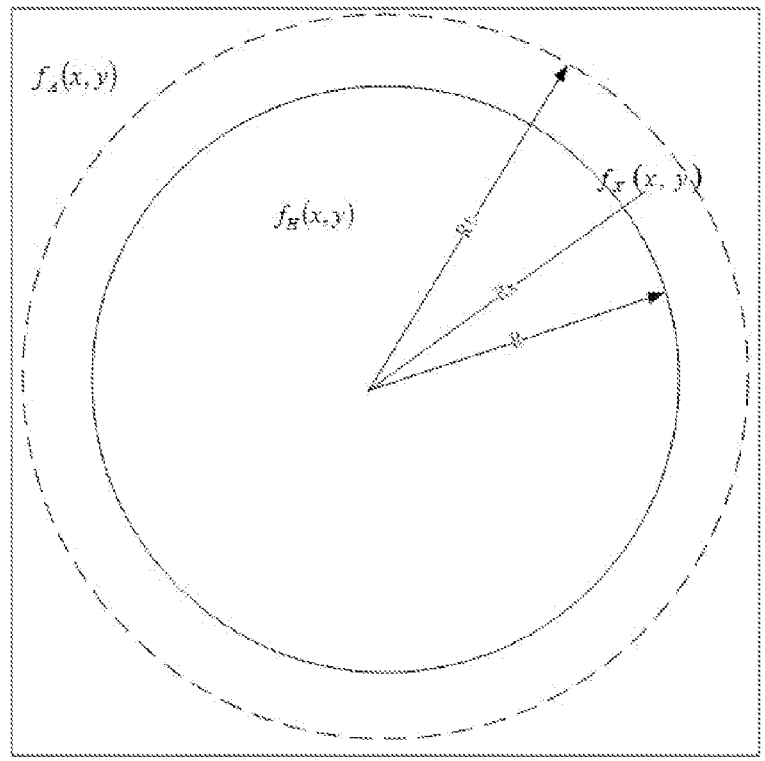
FIG. 4 is a schematic diagram illustrating a processing image region of the method for reconstructing CT scan image according to an example of the present disclosure.

A CT scan image is usually composed of a plurality of small units arranged in a matrix, and the basic units for composing the image are called pixels. The smaller the pixels, the higher the image's resolution, and the higher the image's quality. The artefact usually appears in the truncated region of the reconstructed image, and do not occur in the non-truncated region. In this example, under a condition that the non-truncated region image of the second scan image is guaranteed to be not changed, a processing image region is set in the truncated region, wherein the processing image region means a region which appears an image artefact. In an example, the processing image region may be an annulus. For example, assuming that the region outside the solid circle and inside the dashed circle shown in FIG. 4 is the processing image region. It should be understood that, in this example, the shape of the processing image region is not limited in the present disclosure, and the shape of the processing image region can be determined based on actual situations and requirements.

In this example, the first scan is an axial scan, and the second scan is a helical scan. Please refer to FIG. 4. The block of performing a transition process for pixels of a processing image region in the second scan image based on the first scan image is executed by the following formulas.

$$f_x(x,y) = \left(1 - \frac{Rx - R}{Rt - R}\right) \times f_H(x,y) + \frac{Rx - R}{Rt - R} \times f_A(x,y).$$

Wherein the $f_H(x,y)$ indicates M pixels of the processing image region; the x and the y indicate horizontal axes and vertical axes of the M pixels respectively; the $f_x(x,y)$ indicates pixels of the first scan image corresponding to the M pixels; the $f_x(x,y)$ indicates the M pixels after the transition process; the R indicates a radius of an innermost circle of the processing image region; the Rt indicates a radius of an outermost circle of the processing image region; and the Rx indicates a distance from the M pixels to a center of the processing image region.

In this example, by performing a transition process for pixels of a processing image region in the second scan image based on the first scan image to cover the image artefact, the image artefact can be eliminated so as to effectively improve the quality of reconstructed CT scan image.

Figure 5:
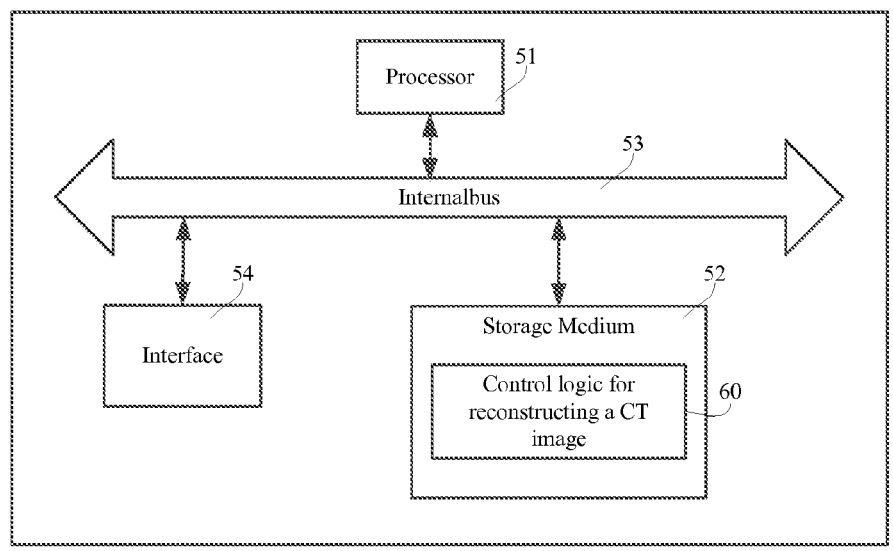
FIG. 5 is a schematic diagram of the hardware architecture of an apparatus for reconstructing CT scan image according to an example of the present disclosure.

Corresponding to the abovementioned methods, an apparatus for reconstructing a CT scan image is provided in the present disclosure. Please refer to FIG. 5. According to an example, the apparatus may include a processor such as a CPU 51 and a machine readable storage medium 52, wherein the processor 51 is connected to the machine readable storage medium 52 through an internal bus 53. In other possible implementations, the apparatus may further include an interface 54 for communicating with other devices or components.

In different examples, the machine readable storage medium 52 may be Random Access Memory (RAM), volatile memory, non-volatile memory, flash memory, storage drives (such as, hard drive), solid state drive, any type of storage disks (such as, CD-ROM, DVD, etc.), or similar storage medium, or a combination thereof.

Figure 6:
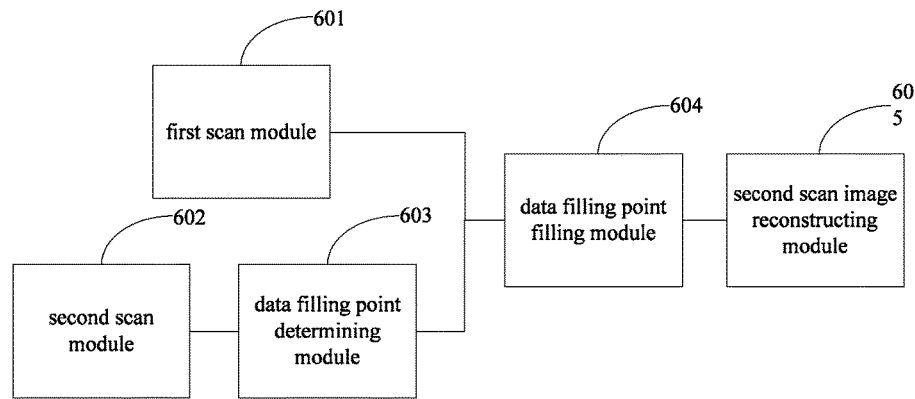
FIG. 6 is a schematic diagram of functional modules of the control logic for reconstructing CT scan image according to an example of the present disclosure.

The machine readable storage medium 52 is used for storing a control logic 60 for reconstructing a CT scan image. As shown in FIG. 6, in functional, the control logic 60 may include a first scan module 601, a second scan module 602, a data filling point determining module 603, a data filling point filling module 604, and a second scan image reconstructing module 605. The first scan module 601 is connected to the data filling point determining module 603, the second scan module 602 is connected to the data filling point determining module 603, the data filling point determining module 603 is connected to the data filling point filling module 604, and the data filling point filling module 604 is connected to the second scan image reconstructing module 605.

The first scan module 601 is to perform a first scan and acquire a first projection data, wherein the first scan is a scan that a subject may be substantially covered by a relatively low dose X-ray beam in an axial plane.

The second scan module 602 is to perform a second scan and acquire a second projection data, wherein the second scan is a scan that a target portion of the subject may be covered by a relatively high dose X-ray beam in the axial plane.

The data filling point determining module 603 is to determine a data filling point of the second projection data, wherein the data filling point may be located in a truncated region.

The data filling point filling module 604 is to fill data of the first projection data corresponding to the data filling point into the data filling point of the second projection data to generate a filled second projection data, based on the theory that assuming the absolute position of a data filling point in the first scan is the same as the absolute position of the data filling point in the second scan, and the so-called absolute position means that the relative positional relationship of the position with respect to a reference point is fixed.

The second scan image reconstructing module 605 is to reconstruct a second scan image based on the filled second projection data, wherein the second scan image is a scan image of the substantially complete subject in the axial plane.

Figure 7:
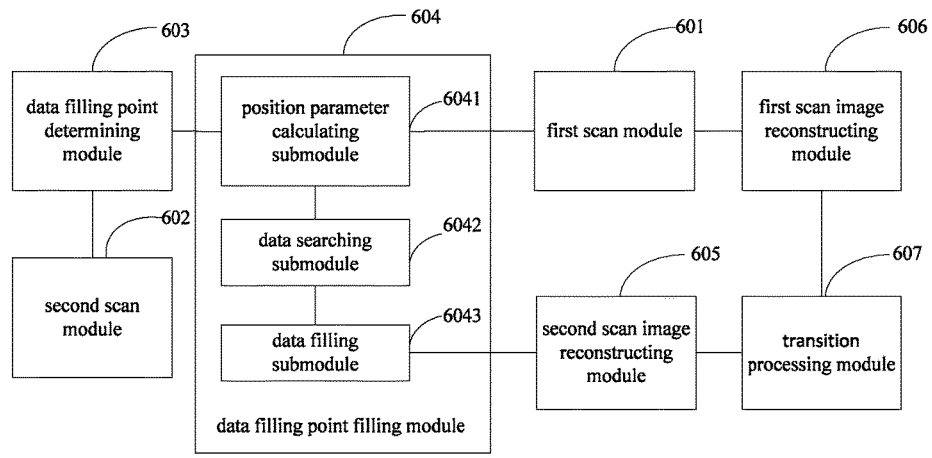
FIG. 7 is a schematic diagram of functional modules of the control logic for reconstructing CT scan image according to another example of the present disclosure.

FIG. 7 is a simplified schematic diagram of functional modules of the control logic for reconstructing CT scan image according to another example of the present disclosure. In this example, the data filling point filling module 604 may further include a position parameter calculating submodule 6041, a data searching submodule 6042, and a data filling submodule 6043. The position parameter calculating submodule 6041 is connected to the data searching submodule 6042, and the data searching submodule 6042 is connected to the data filling submodule 6043.

The first scan module 601 and the data filling point determining module 603 are connected to the position parameter calculating submodule 6041, respectively; and the data filling submodule 6043 is connected to the second scan image reconstructing module 605.

The position parameter calculating submodule 6041 is to calculate a position parameter for the data filling point in the first scan based on a position parameter for the data filling point in the second scan.

The data searching submodule 6042 is configured to search in the first projection data based on the position parameter for the data filling point in the first scan so as to find the data corresponding to the data filling point.

The data filling submodule 6043 configured is to fill the searched corresponding data into the data filling point of the second projection data to generate the filled second projection data.

In the case that the scan types of the first scan and the second scan are different, an image artefact may occur in the truncated region of the second scan image since their ray paths and projection angles of the X-ray beams may differ. Therefore, the control logic 60 may further include a first scan image reconstructing module 606 and a transition processing module 607. The first scan module 601 is connected to the first scan image reconstructing module 606; and the second scan image reconstructing module 605 and the first scan image reconstructing module 606 are connected to the transition processing module 607, respectively.

The first scan image reconstructing module 606 is configured to reconstruct a first scan image based on the first projection data.

The transition processing module 607 is to perform a transition process for pixels of a processing image region in the second scan image based on the first scan image, wherein the processing image region means a region which appears an image artefact.

The example below is implemented with software, which describes how the apparatus runs the control logic 60 for reconstructing a CT scan image. In this example, the control logic 60 of the present disclosure should be understood as machine readable instructions stored in the machine readable storage medium 52. When the processor 51 of the apparatus executes the control logic 60, the processor 51 executes machine readable instructions of the control logic 60 for reconstructing a CT scan image stored in the machine readable storage medium to:

perform a first scan to acquire a first projection data, wherein the first scan is a scan that a subject may be substantially completely covered by a relatively low dose X-ray beam in an axial plane;

perform a second scan to acquire a second projection data, wherein the second scan is a scan that a target portion of the subject may be covered by a relatively high dose X-ray beam in the sectional plane;

determine a data filling point of the second projection data, and fill the data filling point with a data from the first projection data corresponding to the data filling point so as to generate a filled second projection data, wherein the data filling point may be located in a truncated region; and reconstruct a second scan image based on the filled second projection data, wherein the second scan image may be a scan image of the substantially complete subject in the axial plane.

Further, the instructions further cause the processor 51 to:

calculate a position parameter for the data filling point in the first scan based on a position parameter for the data filling point in the second scan;

perform a search in the first projection data based on the position parameter for the data filling point in the first scan so as to find a data corresponding to the data filling point; and fill the corresponding data into the data filling point of the second projection data to generate the filled second projection data.

The position parameter may include a channel index and a slice index of the axial plane.

Further, assuming that a position coordinate for the data filling point in the axial plane of the second scan is (c,r), c indicates a second channel index and r indicates a second slice index; a position coordinate for the data filling point in the axial plane of the first scan is (Ac, Ar), Ac indicates a first channel index and Ar indicates a first slice index, the (Ac, Ar) may be calculated according to the following formulas:

$$ChannelPara = (c - MidC) \times \Delta c;$$

$$Ac = \begin{cases} \dfrac{ChannelPara}{\Delta c} + MidC & \beta' = \beta \\ \dfrac{-ChannelPara}{\Delta c} + MidC & \beta' = \beta \pm \pi \end{cases};$$

$$As = Z_{Channel} + (r - MidR) \times \Delta R;$$

$$Ar = \dfrac{As - Z_1}{\Delta RAxl} + MidAxlR.$$

Wherein the MidC indicates a center channel index of a detector; the $\Delta c$ indicates a channel interval; the ChnnelPara indicates a distance between a channel in that the data filling point is located and a center channel of the detector; the $\beta$ indicates a projection angle of the X-ray beam in the second scan; the $\beta'$ indicates a projection angle of the X-ray beam in the first scan; the $Z_0$ indicates Z-axis coordinate of a projection center of the detector; the $Z_{Channel}$ indicates Z-axis offset representing a distance from the data filling point to the projection center of the detector; the MidR indicates a center slice index of the second scan; the $\Delta R$ indicates a slice interval of the second scan; the As indicates an intermediate variable; the $Z_1$ indicates Z-axis coordinate of the tomography in the first scan that is nearest the data filling point; the MidAxlR indicates a center slice index of the first scan; and the $\Delta RAxl$ indicates a slice interval of the first scan.

Further, when the first scan is an axial scan and the second scan is a helical scan, the Z-axis offset $Z_{Channel}$ may be calculated according to the following formulas:

$$Z_{Channel} = Z_0 + h \times \arcsin \dfrac{ChannelPara}{R};$$

$$h = \dfrac{DetW \times Pitch}{2\pi} \times BedDirection;$$

$$BedDirection = \begin{cases} 1 (\text{foward}) \\ -1 (\text{backward}) \end{cases}.$$

Wherein, the $Z_0$ indicates Z-axis coordinate of the projection center of the detector; the h indicates a bed moving distance that the helical scan scans per 360-degree rotation; the R indicates a scanning radius of the helical scan; the DetW indicates a width of the detector in Z-axis direction; the Pitch indicates a pitch of the helical scan; and the CouchDirection indicates an intermediate variable of a bed moving direction of the helical scan.

Further, the instructions further cause the processor 51 to:

reconstruct a first scan image based on the first projection data; and perform a transition process for pixels of a processing image region in the second scan image based on the first scan image, wherein the processing image region means a region which appears an image artefact.

Wherein the processing image region may be an annulus.

Further, the transition process can be performed according to the following formulas.

$$f_x(x, y) = \left(1 - \frac{Rx - R}{Rt - R}\right) \times f_H(x, y) + \frac{Rx - R}{Rt - R} \times f_A(x, y).$$

Wherein the $f_H(x,y)$ indicates M pixels of the processing image region; the x and the Y indicate horizontal axes and vertical axes of the M pixels, respectively; the $f_A(x,y)$ indicates pixels of the first scan image corresponding to the M pixels; the $f_x(x,y)$ indicates the M pixels after the transition process; the R indicates a radius of an innermost circle of the processing image region; the Rt indicates a radius of an outermost circle of the processing image region; and the Rx indicates a distance from the M pixels to a center of the processing image region.

In this example, by performing a transition process for pixels of a processing image region in the second scan image based on the first scan image to cover an image artefact, the image artefact can be eliminated so as to effectively improve the quality of reconstructed CT scan image.

The figures are illustrations of an example, wherein the units or procedure shown in the figures are not necessarily essential for implementing the disclosure. The units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the disclosure.

Throughout the disclosure, the word "comprise", or variations such as "comprises" or "comprising", will be understood to imply the inclusion of a stated element, integer, block, or group of elements, integers, block, but not the exclusion of any other element, integer or block, or group of elements, integers or blocks.

Numerous variations and/or modifications may be made to the above-described examples, without departing from the broad general scope of the disclosure. The examples are, therefore, to be considered in all respects as illustrative and not restrictive.

The invention claimed is:

1. A method for reconstructing a CT scan image, comprising: performing a first scan to acquire a first projection data, wherein the first scan is a scan that a subject is covered by a low dose X-ray beam in an axial plane;
performing a second scan to acquire a second projection data, wherein the second scan is a scan that a target portion of the subject is covered by a high dose X-ray beam in the axial plane;
determining a data filling point of the second projection data, and filling the data filling point with a data from the first projection data which corresponds to the data filling point so as to generate a filled second projection data, wherein the data filling point is located in a truncated region; and
reconstructing a second scan image based on the filled second projection data, wherein the second scan image is a scan image of the subject in the axial plane;
wherein filling the data filling point with the data from the first projection data which corresponds to the data filling point so as to generate the filled second projection data comprises:
calculating a position parameter for the data filling point in the first scan based on a position parameter for the data filling point in the second scan, wherein the position parameter comprises a channel index and a slice index of the axial plane;
performing a search in the first projection data based on the position parameter for the data filling point in the first scan so as to find a data corresponding to the data filling point; and
filling the corresponding data into the data filling point of the second projection data to generate the filled second projection data.

2. The method according to claim 1, wherein calculating the position parameter for the data filling point in the first scan based on the position parameter for the data filling point in the second scan comprises:
assuming that a position coordinate for the data filling point in the axial plane of the second scan is (c,r), wherein c indicates a second channel index and r indicates a second slice index;
assuming that a position coordinate for the data filling point in the axial plane of the first scan is (Ac, Ar) wherein Ac indicates a first channel index and Ar indicates a first slice index;
calculating the (Ac, Ar) according to the following formulas:

$$ChannelPara = (c - MidC) \times \Delta c;$$

$$Ac = \begin{cases} \dfrac{ChannelPara}{\Delta c} + MidC & \beta' = \beta \\ \dfrac{-ChannelPara}{\Delta c} + MidC & \beta' = \beta \pm \pi \end{cases};$$

$$As = Z_{Channel} + (r - MidR) \times \Delta R;$$

$$Ar = \frac{As - Z_1}{\Delta RAxl} + MidAxlR;$$

wherein the MidC indicates a center channel index of a detector;
the $\Delta c$ indicates a channel interval;
the ChannelPara indicates a distance between a channel in that the data filling point is located and a center channel of the detector;
the $\beta$ indicates a projection angle of the X-ray beam in the second scan;
the $\beta'$ indicates a projection angle of the X-ray beam in the first scan;
the $Z_0$ indicates Z-axis coordinate of a projection center of the detector;
the $Z_{Channel}$ indicates Z-axis offset representing a distance from the data filling point to the projection center of the detector;
the MidR indicates a center slice index of the second scan;
the $\Delta R$ indicates a slice interval of the second scan;
the As indicates an intermediate variable;
the $Z_1$ indicates Z-axis coordinate of the tomography in the first scan that is nearest the data filling point;
the MidAxlR indicates a center slice index of the first scan; and
the $\Delta RAxl$ indicates a slice interval of the first scan.

3. The method according to claim 2, wherein the first scan is an axial scan, and the second scan is a helical scan.

4. The method according to claim 3, wherein the Z-axis offset $Z_{Channel}$ is calculated according to the following formulas:

$$Z_{Channel} = Z_0 + h \times \arcsin\frac{ChannelPara}{R};$$

$$h = \frac{DetW \times Pitch}{2\pi} \times BedDirection;$$

$$BedDirection = \begin{cases} 1(\text{foward}) \\ -1(\text{backward}) \end{cases};$$

wherein, the $Z_0$ indicates Z-axis coordinate of the projection center of the detector;
the h indicates a bed moving distance that the helical scan scans per 360-degree rotation;
the R indicates a scanning radius of the helical scan;
the DetW indicates a width of the detector in Z-axis direction;
the Pitch indicates a pitch of the helical scan; and
the BedDirection indicates an intermediate variable of a bed moving direction of the helical scan.

5. The method according to claim 1, further comprising:
reconstructing a first scan image based on the first projection data; and
performing a transition process for pixels of a processing image region in the second scan image based on the first scan image, wherein the processing image region means a region which appears an image artefact of the second scan image.

6. The method according to claim 5, wherein the processing image region is an annulus.

7. The method according to claim 6, wherein the transition process is performed according to the following formulas:

$$f_x(x, y) = \left(1 - \frac{Rx - R}{Rt - R}\right) \times f_H(x, y) + \frac{Rx - R}{Rt - R} \times f_A(x, y);$$

wherein the $f_H(x,y)$ indicates M pixels of the processing image region;
the x and the y indicate horizontal axes and vertical axes of the M pixels, respectively;
the $f_A(x,y)$ indicates pixels of the first scan image corresponding to the M pixels;
the $f_x(x,y)$ indicates the M pixels after the transition process;
the R indicates a radius of an innermost circle of the processing image region;
the Rt indicates a radius of an outermost circle of the processing image region; and
the Rx indicates a distance from the M pixels to a center of the processing image region.

8. An apparatus for reconstructing a CT scan image, comprising a processor which reads a storage medium storing machine readable instructions corresponding to a control logic for reconstructing CT scan image and executes the machine readable instructions to:
perform a first scan to acquire a first projection data, wherein the first scan is a scan that a subject is covered by a low dose X-ray beam in an axial plane;
perform a second scan to acquire a second projection data, wherein the second scan is a scan that a target portion of the subject is covered by a high dose X-ray beam in the axial plane;
determine a data filling point of the second projection data, and fill the data filling point with a data from the first projection data which corresponds to the data filling point so as to generate a filled second projection data, wherein the data filling point is located in a truncated region; and
reconstruct a second scan image based on the filled second projection data, wherein the second scan image is a scan image of the subject in the axial plane;
wherein when filling the data filling point with the data from the first projection data which corresponds to the data filling point so as to generate the filled second projection data, the machine readable instructions further cause the processor to:
calculate a position parameter for the data filling point in the first scan based on a position parameter for the data filling point in the second scan, wherein the position parameter comprises a channel index and a slice index of the axial plane;
perform a search in the first projection data based on the position parameter for the data filling point in the first scan so as to find a data corresponding to the data filling point; and
fill the corresponding data into the data filling point of the second projection data to generate the filled second projection data.

9. The apparatus according to claim 8, wherein the machine readable instructions further cause the processor to:
assume that a position coordinate for the data filling point in the axial plane of the second scan is (c,r), wherein c indicates a second channel index and r indicates a second slice index;
assume that a position coordinate for the data filling point in the axial plane of the first scan is (Ac, Ar), wherein Ac indicates a first channel index and A indicates a first slice index;
calculate the (Ac, Ar), according to the following formulas:

$$ChannelPara = (c - MidC) \times \Delta c;$$

$$Ac = \begin{cases} \dfrac{ChannelPara}{\Delta c} + MidC & \beta' = \beta \\ \dfrac{-ChannelPara}{\Delta c} + MidC & \beta' = \beta \pm \pi \end{cases};$$

$$As = Z_{Channel} + (r - MidR) \times \Delta R;$$

$$Ar = \frac{As - Z_1}{\Delta RAxl} + MidAxlR;$$

wherein the MidC indicates a center channel index of a detector;
the $\Delta c$ indicates a channel interval;
the ChannelPara indicates a distance between a channel in that the data filling point is located and a center channel of the detector;
the $\beta$ indicates a projection angle of the X-ray beam in the second scan;
the $\beta'$ indicates a projection angle of the X-ray beam in the first scan;
the $Z_0$ indicates Z-axis coordinate of a projection center of the detector;
the $Z_{Channel}$ indicates Z-axis offset representing a distance from the data filling point to the projection center of the detector;
the MidR indicates a center slice index of the second scan;

the ΔR indicates a slice interval of the second scan;
the As indicates an intermediate variable;
the $Z_1$ indicates Z-axis coordinate of the tomography in the first scan that is nearest the data filling point;
the MidAxlR indicates a center slice index of the first scan; and
the ΔRAxl indicates a slice interval of the first scan.

10. The apparatus according to claim 9, wherein the first scan is an axial scan, and the second scan is a helical scan.

11. The apparatus according to claim 10, wherein the Z-axis offset $Z_{Channel}$ is calculated according to the following formulas:

$$Z_{Channel} = Z_0 + h \times \arcsin\frac{ChannelPara}{R};$$

$$h = \frac{DetW \times Pitch}{2\pi} \times BedDirection;$$

$$BedDirection = \begin{cases} 1(\text{foward}) \\ -1(\text{backward}) \end{cases};$$

wherein, the $Z_0$ indicates Z-axis coordinate of the projection center of the detector;
the h indicates a bed moving distance that the helical scan scans per 360-degree rotation;
the R indicates a scanning radius of the helical scan;
the DetW indicates a width of the detector in Z-axis direction;
the Pitch indicates a pitch of the helical scan; and
the BedDirection indicates an intermediate variable of a bed direction of the helical scan.

12. The apparatus according to claim 8, wherein the machine readable instructions further cause the processor to:
reconstruct a first scan image based on the first projection data; and
perform a transition process for pixels of a processing image region in the second scan image based on the first scan image, wherein the processing image region means a region which appears an image artefact of the second scan image.

13. The apparatus according to claim 12, wherein the processing image region is an annulus.

14. The apparatus according to claim 13, wherein the machine readable instructions further cause the processor to perform the transition process according to the following formulas:

$$f_x(x, y) = \left(1 - \frac{Rx - R}{Rt - R}\right) \times f_H(x, y) + \frac{Rx - R}{Rt - R} \times f_A(x, y);$$

wherein the $f_H(x,y)$ indicates M pixels of the processing image region;
the x and the y indicate horizontal axes and vertical axes of the M pixels, respectively;
the $f_A(x,y)$ indicates pixels of the first scan image corresponding to the M pixels;
the $f_x(x,y)$ indicates the M pixels after the transition process;
the R indicates a radius of an innermost circle of the processing image region;
the Rt indicates a radius of an outermost circle of the processing image region; and
the Rx indicates a distance from the M pixels to a center of the processing image region.

\* \* \* \* \*